United States Patent [19]

Parrotta, Jr. et al.

[11] Patent Number: 4,900,542

[45] Date of Patent: Feb. 13, 1990

[54] MANUFACTURING PROCESS FOR MICROCRYSTALLINE EMULSIONS

[75] Inventors: Umberto V. Parrotta, Jr., Hamilton Township, Mercer County; Gianluigi Soldati, Edison; Frederick P. Sisbarro, Wayne, all of N.J.

[73] Assignee: Carter-Wallace Inc., New York, N.Y.

[21] Appl. No.: 62,742

[22] Filed: Jun. 15, 1987

Related U.S. Application Data

[63] Continuation-in-part of Ser. No. 713,933, Mar. 20, 1985, Pat. No. 4,673,570.

[51] Int. Cl.$^4$ .......................... A61K 7/32; A61K 7/34; A61K 7/38
[52] U.S. Cl. ........................................ 424/66; 424/68; 514/937; 514/938; 514/944
[58] Field of Search ..................... 424/68, 66

[56] References Cited

U.S. PATENT DOCUMENTS

| | | | |
|---|---|---|---|
| 3,903,258 | 9/1975 | Siegal | 424/68 |
| 4,499,069 | 2/1985 | Krafton | 424/68 |
| 4,517,176 | 5/1985 | Felger | 424/68 |
| 4,673,570 | 6/1987 | Soldati | 424/66 |

*Primary Examiner*—Dale R. Ore
*Attorney, Agent, or Firm*—Kevin B. Clarke

[57] ABSTRACT

A batch process and continuous/semicontinuous processes for the manufacture of uniform, clear, microcrystalline emulsion compositions of gel-like consistency are disclosed.

6 Claims, 3 Drawing Sheets

MANUFACTURING PROCESS FOR MICROCRYSTALLINE EMULSIONS

BACKGROUND

Antiperspirants and deodorants generally available are in the form of aerosol suspensions, roll-on powders, emulsions and solids.

Clear antiperspirants have been attempted, but to date, none has reached the market place. It is believed that a clear antiperspirant product which offers efficacy and aesthetic properties equal to or better than products presently available would be well received by the purchasing public.

Clear stick deodorant compositions have been available for some time. The clear sticks are generally produced by using stearate soaps as gelling agents for an alcoholic or gylcolic solution of an anti-microbial agent and a fragrance. These deodorant products offer no antiperspirant protection. The use of antiperspirant active ingredients, which are cationic in nature, in the aforesaid deodorant compositions, is chemically incompatible due to the chemical interaction/inactivation between the antiperspirant active material and the soap.

Products of gel consistency can be achieved through the use of gelling agents such as cellulosic or algin derived polymeric materials. Synthetic resins can also be utilized. These materials however are incompatible with electrolites (antiperspirants salts) especially at the levels required for antiperspirant efficacy and at the low pH regime of these preparations. "Gelling agents" work on the concept that when these polymeric materials dissolve or swell in water or other mediums at a sufficient high concentration form gel like products. These are not emulsions. The gel is formed when the gellant crystals are forced out of solution in very fine particle size. These crystals interlock in quiescent state to give the gel its body.

Some cellulosic materials, such as hydroxypropylcellulose, among others, are compatible with polyvalent metal salts and have been used in the manufacture of clear lotions. These cellulosic materials, however, must be prepared with a high percentage of water or alcohol in order to insure solubilization of the active ingredient. Such formulations, in addition to a high irritation potential, are tacky and pituitous and low in efficacy when alcohol based, and exhibit tackiness and long drying time when water based.

A second way of preparing gel type product involves the use of hydrophilic surfactants at sufficiently high levels in aqueous solutions. These products, prepared with conventional surfactants will solubilize oils. Normally they are slow drying and not too aesthetic. In addition, due to the high level of non volatiles, these are also expected to have low antiperspirant efficacy.

We have developed a clear microcrystalline emulsion of gel consistency without the use of gelling agents nor conventional emulsifiers/surfactants. We were able to do so with low levels of unique silicone emulsifiers. Furthermore the microcrystalline emulsion is aesthetically pleasing, fast drying and is an effective antiperspirant.

Wax and soap-gel and gelled antiperspirant sticks are disclosed in various United States patents i.e. U.S. Pat. Nos. 4,382,079; 4,414,200; 4,280,994; 4,265,878, 3,259,545; 2,970,083; 2,933,433; 2,900,306; 2,857,315 and 4,383,988.

Gelled antiperspirants have been disclosed in U.S. Pat. No. 4,383,988.

SUMMARY

It has now been found that uniform, clear microcrystalline emulsion antiperspirant compositions of gel-like consistency which do not contain waxes nor conventional gelling agents such as soaps, cellulosics or alginates can be prepared. The stable gel emulsions of the present invention are easily applied to the skin and have a smooth, slippery feel yet are fast drying and nontacky.

The compositions prepared in accordance with the procedures of the present invention are microcrystalline emulsions of gel-like consistency comprising in combination a volatile silicone fluid, a silicone emulsifier, a destabilizing auxiliary emulsifier, water, a non-volatile emollient, a coupling agent, an active antiperspirant component and ancillary agents such as perfume, coloring agents etc.

The compositions of the present invention may be prepared by batch process, continuous or semi-continuous process and yield formulations which are stable, highly efficaceous and possess excellent aesthetic qualities.

DETAILED DESCRIPTION

Antiperspirant microcrystalline emulsion compositions of the present invention do not contain waxes nor conventional gelling agents such as cellulosic, nor gums.

The compositions prepared in accordance with the procedures of the present invention are clear microcrystalline emulsions of gel-like consistency which comprise unique silicone emulsifiers, the preferred being a cyclomethicone and dimethicone copolyol silicone fluid having a viscosity at 25 C. (77 F.) of 100-3000 cps. Such copolyols among others are marketed by Dow Corning Corporation under the trademark DOW CORNING 3225 Formulation Aid.

The silicone emulsifier as marketed is present in the compositions of the present invention in amounts ranging from about 10% by weight of the total composition to about 25% by weight of the total composition. The emulsifier composition is preferably present in amounts of from 15% to 25% by weight of the total composition.

Emolliency and detackifying properties are imparted to the compositions of the present invention by the addition of volatile silicones composed of low molecular weight polydimethylcyclosiloxanes that have been assigned the CTFA name cyclomethicone and are exemplified by the formula:

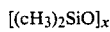

$$[(CH_3)_2SiO]_x$$

wherein x is an integer of from about 4 to 6. Highly preferred cyclic siloxanes are octamethylcyclotetrasiloxane (x=4), decamethylcyclopentasiloxane (x=5) and blends of tetramer and pentamer cyclomethicone. Commercial cyclic siloxanes are readily available from manufacturers such as Union Carbide's Trademarked product Volatile Silicone 7207,7158 and the following Trademarked products of Dow Corning Corporation; Dow Corning 344 Fluid and Dow Corning 345 Fluid; SWS Silicone Corporation, Silicone Fluid F222, F263 and 03314; and G.E. Company SF1173, SF1202.

Desirably the volatile silicones employed in the compositions of the present invention are present in amounts of from about 10% to about 60% by weight of the total composition preferably from 11% to 16% by weight.

A further component of the compositions of the present invention is selected from among the non-volatile emollient materials and mixtures thereof. Such materials in addition to their emollient properties reduce the whitening action of the cyclomethicones. The non-volatile emollient is present in amount of from about 1% by weight to about 10% by weight of the total composition preferably from about 1% to about 5% by weight.

The non-volatile emollient is selected from among the higher alkyl fatty acid esters and ethers, i.e. those having fatty acid chains of from 10 to 20 carbon atoms, linear silicone fluids, polyalkylene glycols, lanolin, lanolin alcohol and mineral oil. The preferred non-volatiles are selected from isopropyl myristate, isopropyl palmitate, diisopropyl and dicapryl adipate, ethyl hexyl isononate, dimethicone or other polydimethylsiloxanes, PPG-20 methyl glucose ether, PPG-14 butyl ether, PPG-15 stearyl ether, mineral oil (and) lanolin alcohol. The non-volatile emollients can be used independently or in combination within the above-noted ranges.

An additional component of the compositions of the present invention is a coupling agent selected from the low molecular weight, i.e. 2 to about 8 carbon atom alcohols such as ethanol and glycols such as propylene glycol, dipropylene glycol and polyethylene glycol which is present in amounts of from about 2% by weight of the total composition to about 10%. The coupling agent is preferably present in amounts of from 3.5% to 6.5% by weight.

The active antiperspirant material utilized in the compositions of the present invention is in powder form, or pre-dissolved in water, and may be buffered or unbuffered. Preferred antiperspirant materials are aluminum chlorohydrate, aluminum zirconium trichlorohydrate, tetrachlorohydrate or octachlorohydrate, aluminum sesquichlorohydrate and complexes thereof. The antiperspirant materials are present, in powder form, in amounts of from about 15% by weight of the total composition to about 30% by weight of the total composition preferably from about 20% to about 25% by weight.

Desirably, the compositions of the present invention also contain a auxiliary emulsifier in amounts of from about 0.5% to about 2% by weight of the total composition. Not wishing to be bound by any theory, it is believed that their use in combination with the volatization of the silicones destabilizes the emulsion, thus enhancing the efficacy of the composition.

The balance of the compositions of the present invention, approximately 30% to about 50% by weight, is deionized water. It being understood that additional materials, which are well-known in the antiperspirant art, such as fragrances, bactericides, fungicides, skin treating and conditioning materials etc. may be included in minor amounts in the compositions.

Examples, not to be considered as limiting, of the gel-antiperspirant formulations prepared in accordance with the procedures of the present invention are described below:

| Example # | I WT. % | II WT. % | III WT. % | IV WT. % | V WT. % | VI WT. % | VII WT. % | VIII WT. % | IX WT. % |
|---|---|---|---|---|---|---|---|---|---|
| Cyclomethicone | 11.00 | 15.50 | 15.50 | 11.00 | 15.50 | 14.50 | 14.50 | 15.50 | 10.25 |
| Cyclomethicone (and) Dimethicone Copolyol | 15.00 | 20.00 | 15.00 | 15.00 | 20.00 | 20.00 | 20.00 | 20.00 | 20.0 |
| P.E.G.-4 Oleate | — | 1.00 | — | — | — | 1.00 | 1.00 | — | 1.00 |
| Laureth-23 | 1.50 | — | 1.50 | 1.50 | 2.00 | — | — | 2.00 | 1.00 |
| Ethanol | 3.50 | 4.00 | 4.00 | 3.50 | — | — | 4.00 | — | — |
| Propylene Glycol | — | — | — | — | — | 4.00 | — | 6.50 | 4.00 |
| Polydimethyl Siloxane | — | — | — | 2.00 | 2.00 | — | — | 1.50 | 1.00 |
| Isopropyl Myristate | 3.00 | — | — | 3.00 | — | — | — | — | — |
| Isopropyl Palmitate | — | — | — | — | 1.00 | — | — | 1.00 | — |
| PPG-15 Stearyl Ether | 2.00 | — | — | — | — | — | — | — | — |
| Mineral Oil (and) Lanolin Alcohol | — | — | — | — | — | 1.00 | 1.00 | — | 2.50 |
| Aluminum Chlorohydrate | 21.00 | 21.00 | — | — | — | — | — | — | — |
| Aluminum Zirconium Tetrachlorohydrex Gly | — | — | — | — | — | 21.00 | 21.00 | — | 21.00 |
| Aluminum Zirconium Octachlorohydrex Gly | — | — | 21.00 | 21.00 | 22.00 | — | — | 22.00 | — |
| Water | 42.50 | 38.00 | 42.50 | 42.50 | 37.00 | 38.00 | 38.00 | 31.50 | 38.50 |
| Perfume | 0.50 | 0.50 | 0.50 | 0.50 | 0.50 | 0.50 | 0.50 | 0.50 | 0.75 |

The compositions of the present invention may be prepared by a batch process which comprises mixing the antiperspirant active material with water and charging this aqueous phase into the oil-alcohol phase containing the volatile silicone, the silicone emulsifier, the non-volatile emollient, the coupling agent and other non-aqueous components and heating the mixture at about 25 C. to about 45 C. with agitation until uniform, then homogenizing.

Alternatively, the compositions of the present invention may be prepared by a continuous/semicontinuous process wherein a metering/proportioning pump is added to the batch process in order to minimize capital outlay, product loss, batch to batch variation, handling problems and to build in viscosity and/or product set-up prior to filling.

BRIEF DESCRIPTION OF DRAWINGS

The invention will be further described with respect to the accompanying drawings wherein.

It is to be understood the invention described with respect to the drawings is for purposes of illustration only, and the invention is not to be limited to the particular embodiment shown in such drawings. Moreover, it is to be understood that various equipments such as valves, controllers and the like have not been completely shown, and the placing of appropriate equipment at appropriate places is within the scope of knowledge of those skilled in the relevent arts.

Figure 1:
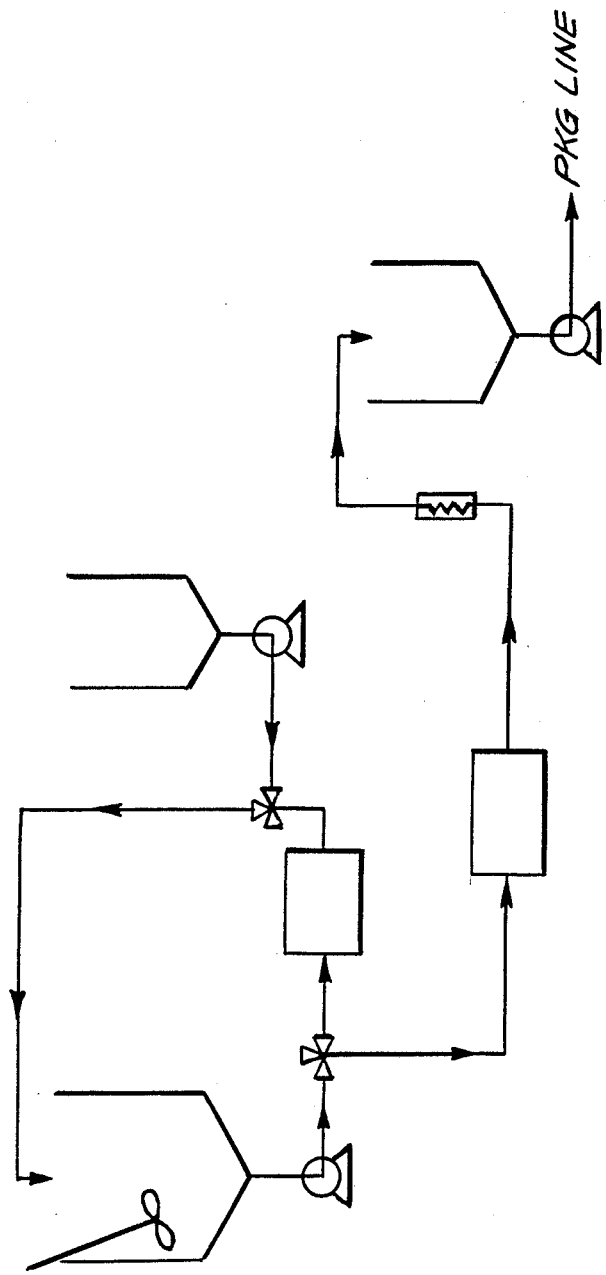
FIG. 1 is a simplified schematic flow diagram of a batch process for producing the uniform, clear microcyrstalline emulsion compositions of the present invention.

Referring now to FIG. 1 of the drawings, the aqueous phase is prepared by charging the required amount of deionized water into tank 10, agitation is begun and water soluble powdered antiperspirant active is slowly charged into the deionized water. This step may be eliminated if an aqueous solution of antiperspirant active is charged into tank 10 in lieu of powdered antiperspirant active. Kettle II, equipped with sweep blades turbine; propellar or other conventional mixing means well known in the art is charged with volatile silicone followed by a silicone emulsifier and agitation is begun followed by the addition of non-volatile emollients, fragrance and a coupling agent.

The aqueous phase in supply tank 10 is fed through lines 13 and 14 including suitable valves and pumps, into Kettle 11 where agitation is increased and continued until the mixture is uniform. Heating of the contents of Kettle 11 is commenced and continued at about 20 C. to about 80 C. at which point it is held and recycling under pressure of the contents of Kettle 11 by way of lines 14, 15 and 16, including suitable valves and pumps, optionally through mill 17, is begun. Mill 17 may be a Greer Mill, a colloid mill, high speed dispenser, pipe line mixer, static mixer, etc. Recycling with or without back pressure can be continued for about one (1) hour. Recycling may be stopped or continued while product is transferred by way of line 18, including suitable valves and pumps, to a high energy imput device 19 such as a high pressure homogenizer and every input/homogenization is commenced. Examples of suitable pressures to be used in the energy imput/homogenization process using a high pressure homo such as a Gaulin in order to obtain the desired, clear, uniform microcrystalline emulsion antiperspirant compositions of gel-like consistency of the present invention range from 100 psig to 10,000 psig.

The energy imput/homogenization can be carried out while the product is transferred by recycling or for a period of about one (1) hour and the product is then transferred by way of lines 20 and 22 including suitable valves and pumps through heat exchanger 21 to holding tank 23.

Figure 2:
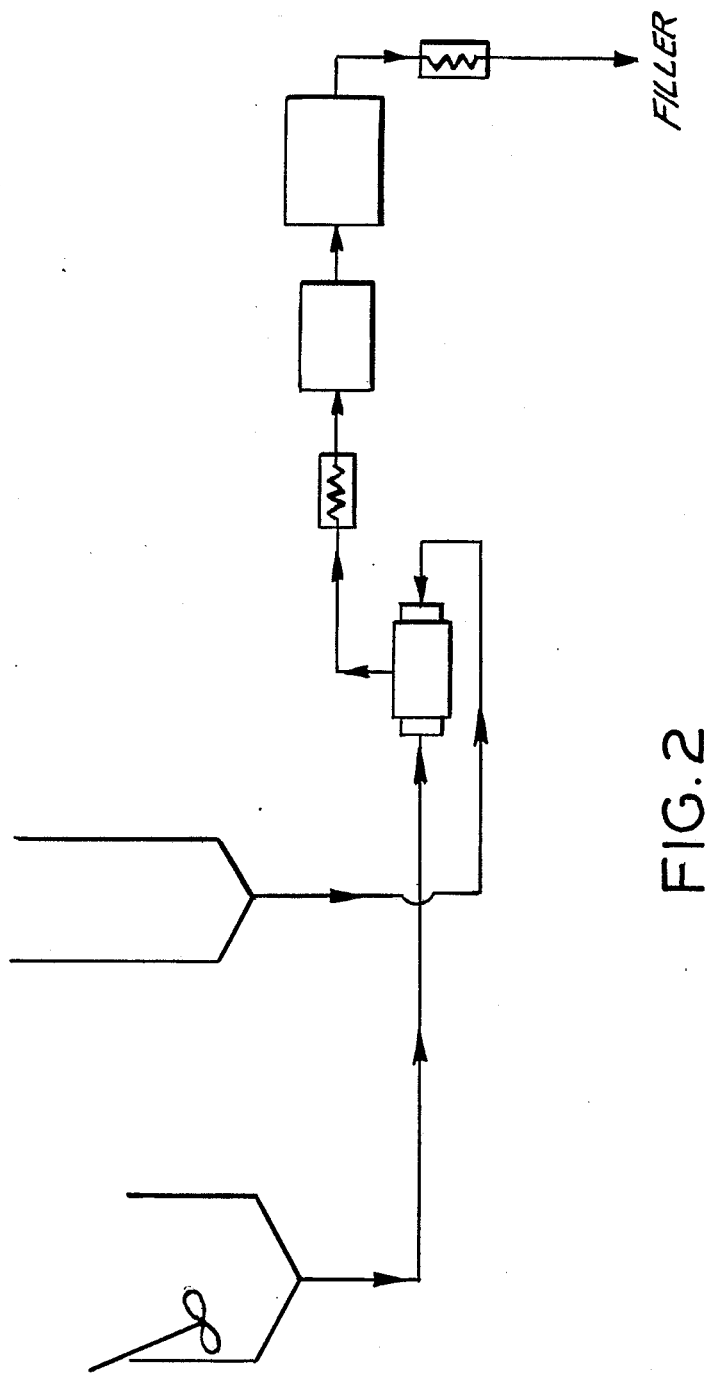
FIG. 2 is a simplified schematic flow diagram of a continuous/semicontinuous process for producing the uniform, clear, microcrystalline emulsion compositions of the present invention.

As shown more particularly in FIG. 2 of the drawings, the process of the present invention may be operated in a continuous or semicontinuous manner wherein a metering/proportioning pump 24 receives the aqueous phase through line 25 and the oil phase through line 26, the aqueous phase and oil phase combines in suitable proportions flows through line 26 and heat exchanger 27 to optional mill 17 and homogenizer 19 as described in connection with FIG. 1 above.

Figure 3:
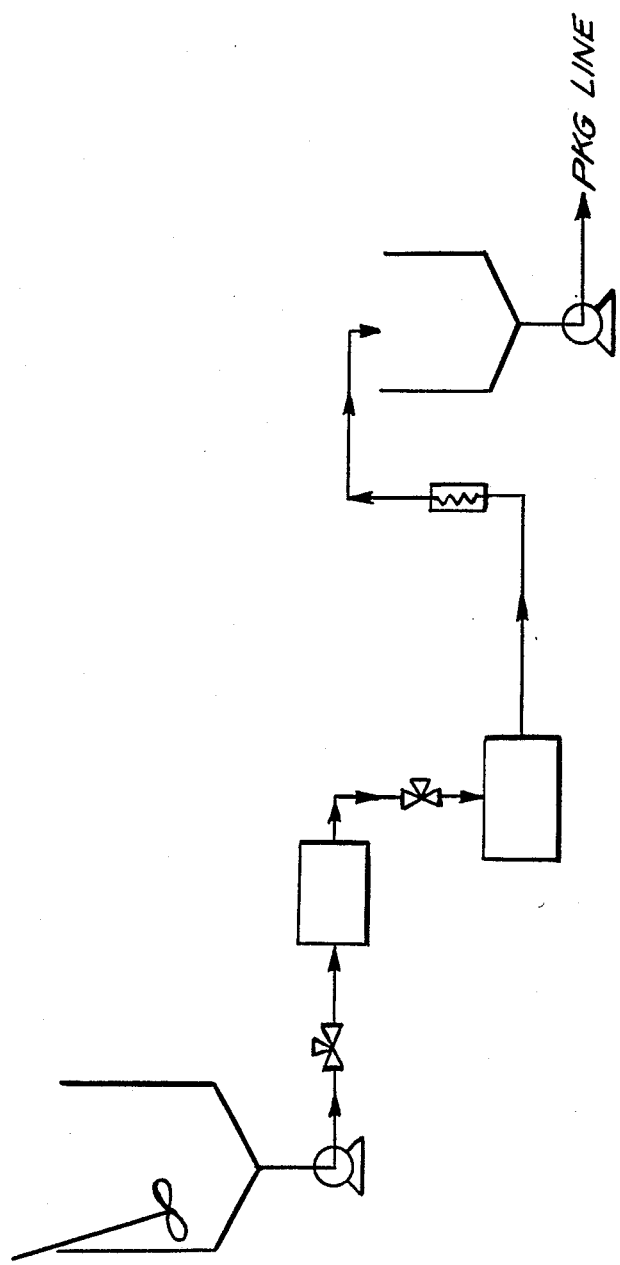

In accordance with a particularly preferred embodiment depicted in FIG. 3 of the drawings, the present invention is directed to the production of uniform, clear, gel-like antiperspirant-deodorant microcrystalline emulsions from compositions which are free of waxes and conventional gelling agents and which are basically comprised of an aqueous phase containing dissolved antiperspirant active and an oil phase composed of a silicone emulsifier, a volatile silicone, a non-volatile emollient and a coupling agent.

As described in FIG. 3, the oil-alcohol phase is made up in Kettle 11, which contains the silicones, etc. the water is added to this phase forming an opaque lotion-like emulsion. The antiperspirant active is then added, which at this point begins formation of a thin translucent micro emulsion.

Heating of the batch is then commenced to a temperature ranging from about 25 C. to about 45 C. When the batch has attained the desired temperature, the batch is optionally passed through a mill with or without pressure and subsequently passed through to a high pressure homogenizer 19 via Line 18A. The homogenization process is accomplished at a pressure ranging from 1,00 psig to about 10,000 psig. A gel-like micro emulsion is formed. The batch may be held in holding vessel 23 or passed directly to a filler.

The clear, uniform microcrystalline emulsion antiperspirants of the present invention were effectively formed without conventional gelling agents or waxes.

Numerous modifications and variations of the present invention are possible in light of the above teachings and therefore within the scope of the appended claims. It is understood that the invention may be practiced in a manner other than as particularly described.

What is claimed:

1. A process for preparing uniform, clear, microcrystalline emulsion antiperspirant compositions of gel-like consistency comprising:

mixing the antiperspirant active material with water, charging said aqueous phase into an oil-alcohol phase containing a volatile silicone, a silicone emulsifier, a non-volatile emollient and a coupling agent, heating the resultant mixture with agitation until a uniform mixture is obtained, homogenizing said mixture and passing said homogenized mixture to a holding tank or directly to a filter.

2. The process of claim 1 wherein said mixture is heated to a temperature of from about 25° C. to about 45° C.

3. The process of claim 1 wherein said homogenization is accomplished at a pressure of from about 1,000 psig to about 10,000 psig.

4. The process of claim 1 wherein said heated mixture is milled prior to homogenization.

5. The process of claim 1 which is a batch process.

6. The process of claim 1 which is a continuous process.

* * * * *